US00PP32618P3

(12) United States Plant Patent
Green et al.

(10) Patent No.: US PP32,618 P3
(45) Date of Patent: Dec. 15, 2020

(54) APPLE TREE NAMED 'RDS'

(50) Latin Name: *Malus domestica*
Varietal Denomination: RDS

(71) Applicants: Ashley Green, Lenswood (AU); Brenton Green, Lenswood (AU)

(72) Inventors: Ashley Green, Lenswood (AU); Brenton Green, Lenswood (AU)

(73) Assignee: Fruit Varieties International Pty Ltd, Grove (AU)

( * ) Notice: Subject to any disclaimer, the term of this patent is extended or adjusted under 35 U.S.C. 154(b) by 18 days.

(21) Appl. No.: 16/350,662

(22) Filed: Dec. 17, 2018

(65) Prior Publication Data

US 2019/0191610 P1 Jun. 20, 2019

(51) Int. Cl.
*A01H 6/74* (2018.01)
*A01H 5/08* (2018.01)

(52) U.S. Cl.
USPC ..... Plt./161
CPC ..... *A01H 6/7418* (2018.05)

(58) Field of Classification Search
USPC ..... Plt./156, 161
See application file for complete search history.

(56) References Cited

PUBLICATIONS

UPOV-PLUTO: Plant Variety Database, Sep. 12, 2019, citation for 'RDS'. 1 page.*

* cited by examiner

*Primary Examiner* — Susan McCormick Ewoldt
*Assistant Examiner* — Karen M Redden
(74) *Attorney, Agent, or Firm* — Phase M Legal

(57) ABSTRACT

A new and distinct apple tree *Malus domestica* named 'RDS'.'RDS' is a spontaneous limb mutation of the variety 'Cripps Red' and is distinguished by its early color development, a reddish brown current season wood growth on the sunny side, and a high level of red anthocyanin on the back of the leaf petiole and on young fruitlets. It is further distinguished by its strong bloom on fruit at maturity, a very dark intensity purple red hue of overcolor and a narrow stripe with solid flush having weakly defined stripes overcolor.

7 Drawing Sheets

Latin name of the genus and species: Botanical classification: *Malus domestica.*

Variety denomination: The new apple tree variety denomination is 'RDS'.

BACKGROUND OF THE VARIETY

The present invention is a new and distinct cultivar of apple tree botanically known as *Malus domestica* and referred to by the cultivar name 'RDS'. 'RDS' was discovered as a spontaneous limb mutation in a commercial orchard of the variety 'Cripps Red' (also known as 'Cripps-Two' (U.S. Plant Pat. No. 8,477)).

'RDS' was first observed in 2013 in Lenswood, South Australia, Australia, where it was distinguished by its dark purple red fruit color. 'RDS' is further distinguished from its parent by its early color development: reddish brown current season wood growth on the sunny side with a high level of red anthocyanin on the back of the leaf petiole and a high level of red anthocyanin on young fruitlets. It is further distinguished by a strong bloom on fruit at maturity, a very dark intensity purple red hue overcolor, and a narrow stripe with solid flush overcolor. Asexual reproduction of 'RDS' was carried out by bud grafting in 2014 and trees of 'RDS' were planted for additional observation at Lenswood, South Australia, Australia. 'RDS' has since been fruited through successive asexually propagated generations at Lenswood, South Australia and has been observed to remain true to type with the distinguishing characteristics retained through successive generations of asexual reproduction.

BRIEF DESCRIPTION OF THE VARIETY

'RDS' is primarily distinguished by its dark purple red fruit color. 'RDS' is also distinguished from its parent by its early color development: a reddish brown current season wood growth on the sunny side, a high level of red anthocyanin on the back of the leaf petiole, and a high level of red anthocyanin on young fruitlets. 'RDS' also exhibits a strong bloom on fruit at maturity, a very dark intensity purple red hue overcolor and a narrow stripe with solid flush having weakly defined stripes overcolor. These and other distinguishing characteristics are set forth in the tables below. Under similar growing conditions in Tasmania, Australia, under commercial practice, 'RDS' is distinguishable from its parent 'Cripps Red' as described in Table 1 below:

TABLE 1

Comparison of 'RDS' to 'Cripps Red' (also known as 'Cripps-Two' (U.S. Plant Pat. No. 8,477))

| Characteristic | 'Cripps Red' | 'RDS' |
|---|---|---|
| Fruit: Relative Area of Overcolor | Medium to Large | Very Large |
| Fruit: Hue of Overcolor with Bloom removed | Red-purple 60A | Red-purple 59A |

TABLE 1-continued

Comparison of 'RDS' to 'Cripps Red' (also known as 'Cripps-Two' (U.S. Plant Pat. No. 8,477))

| Characteristic | 'Cripps Red' | 'RDS' |
|---|---|---|
| Fruit: Intensity of Overcolor | Light to Medium | Dark |
| Fruit: Width of Stripes | Medium to broad | Very narrow to Narrow |
| Young Fruit: Extent of Anthocyanin Over color | Very small to small - 21% on average of fruitlet covered with Anthocyanin | Large - 61% on average of fruitlet covered with Anthocyanin |
| Petiole: Extent of Anthocyanin coloration from base | Small - 4.40 mm on average | Large - 21.90 mm on average |
| 1 Year Old Shoot: Sun Exposed Side Color | Medium-brown 165B | Reddish-brown 181A |
| 1 Year Old Shoot: Number of Lenticels | Medium - 95 on average per 100 mm of stem | Very few to few - 78 on average per 100 mm of stem |

'RDS' is also distinguishable from similar well-known commercial variety 'Cripps Pink' (U.S. Plant Pat. No. 7,880) as described in Table 2 below. Under similar growing conditions in Tasmania, Australia, under commercial practice, 'RDS' is primarily distinguished from 'Cripps Pink' by its dark purple red fruit color, particularly its very large and dark intensity of overcolor, and the heavy extent of bloom on the mature fruit surface. 'RDS' is also distinguished from 'Cripps Pink' by its large extent of petiole anthocyanin compared to 'Cripps Pink', its globose fruit shape and its later time for harvest. These and other distinguishing characteristics are set forth in the table below.

TABLE 2

Comparison of 'RDS' to 'Cripps Pink' (U.S. Plant Pat. No. 7,880)

| Characteristic | 'Cripps Pink' | 'RDS' |
|---|---|---|
| One-year-old shoot on Sunny Side | Light-Brown 174A | Reddish-Brown 181A |
| Petiole Anthocyanin | Small | Very Large |
| Young Fruit Anthocyanin | Absent/Small | Medium |
| Fruit - Area of Overcolor | Small | Very Large |
| Fruit - Intensity of Overcolor | Light | Dark |
| Fruit - Extent of Bloom on Mature Fruit Surface | Absent to Very Light if any | Present and Heavy Bloom |
| Fruit - Time for Harvest | Late | Very Late |
| Fruit - Width of Stripes | Medium | Very Narrow to Narrow |
| Fruit - Shape | Cylindrical | Globose |
| One-Year-Old Shoot - Number of Lenticels | 140 average per 100 mm of stem - Many | 78 average per 100 mm of stem - Medium |
| Tree - Habit Growth Pattern of Branches | Upright | Spreading |

BRIEF DESCRIPTION OF THE PHOTOGRAPHS

Typical specimens of the tree and blossoms for the new apple tree variety 'RDS' of a 3-year-old tree planted on 'MM106' rootstock (not patented) are shown in the accompanying photographs. The colors shown are as true as possible within the usual limits of this kind of illustration.

DETAILED BOTANICAL DESCRIPTION OF THE VARIETY

Figure 1:
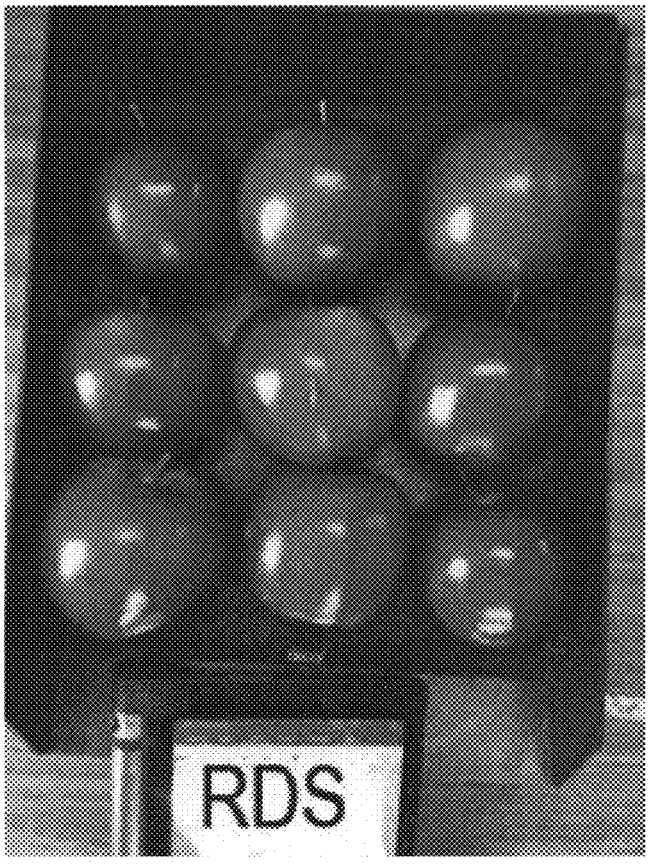
FIG. 1 shows current season's fresh fruit of 'RDS' harvested at maturity.
Figure 2:
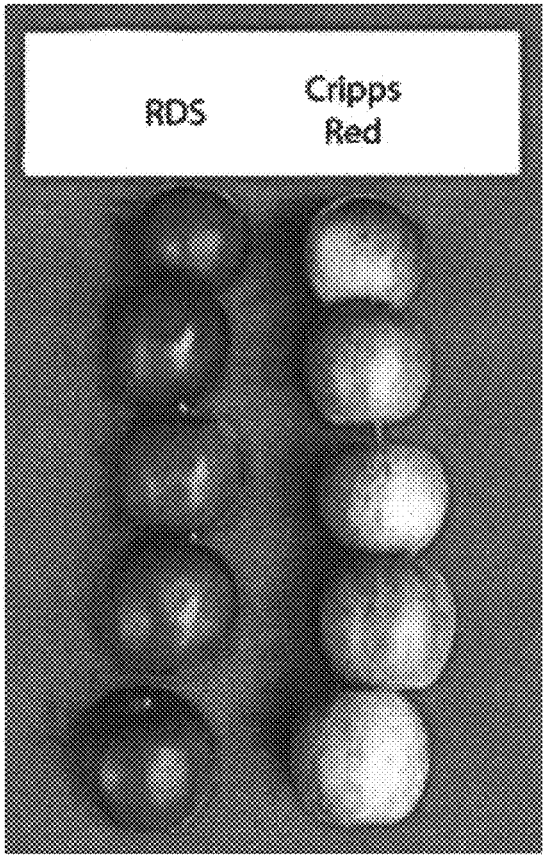
FIG. 2 shows current season's fresh fruit of 'RDS' (on the left) compared to fruit of 'Cripps Red' (on the right), both harvested at maturity from trees of similar age and growing conditions.
Figure 3:
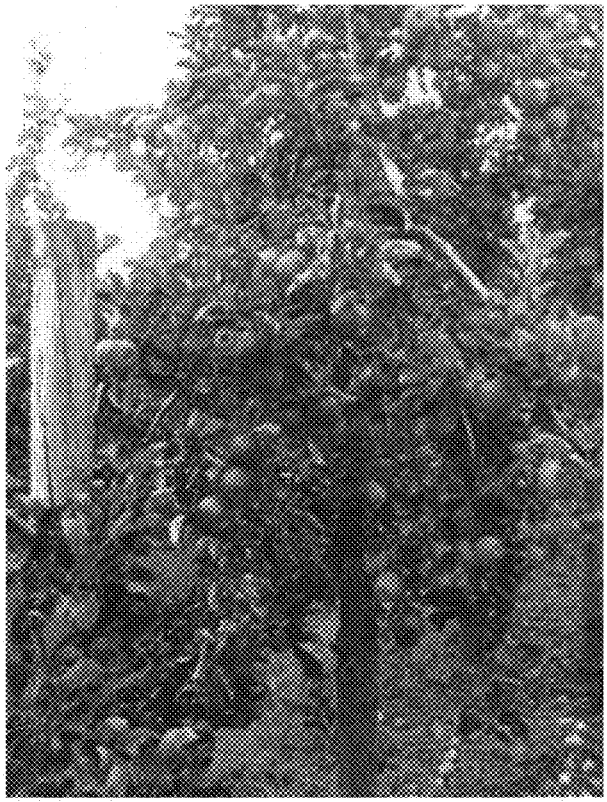
FIG. 3 shows the parent tree 'Cripps Red' and early color development of 'RDS' limb sport.
Figure 4:
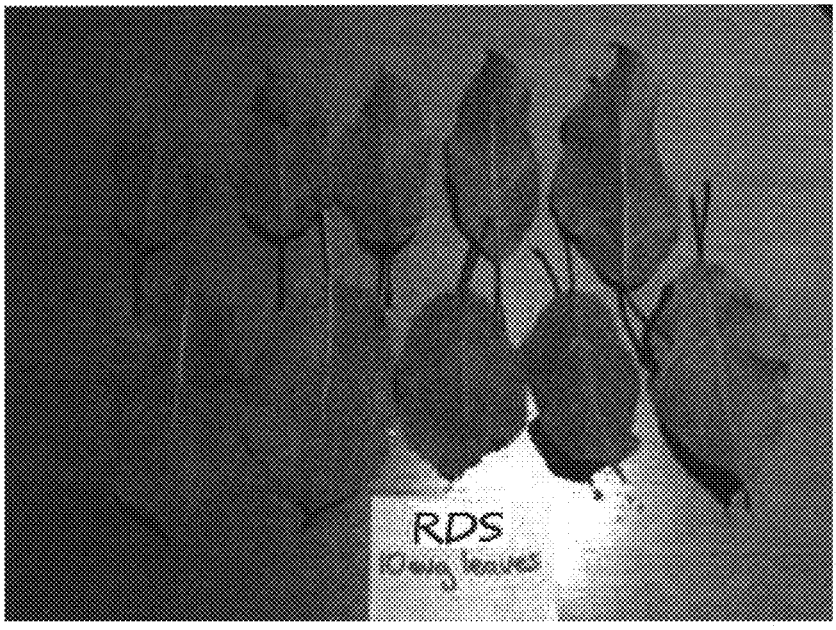
FIG. 4 shows the under-side of leaves of a 3-year-old current season's shoot of 'RDS' in its third growing season on 'MM106' rootstock.
Figure 5:
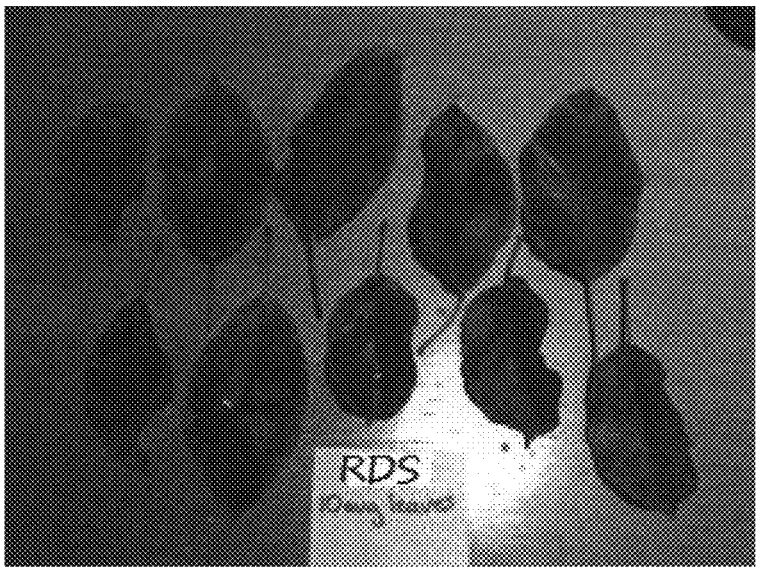
FIG. 5 shows the upper-side of leaves of a 3-year-old current season's shoot of 'RDS' in its third growing season on 'MM106' rootstock.
Figure 6:
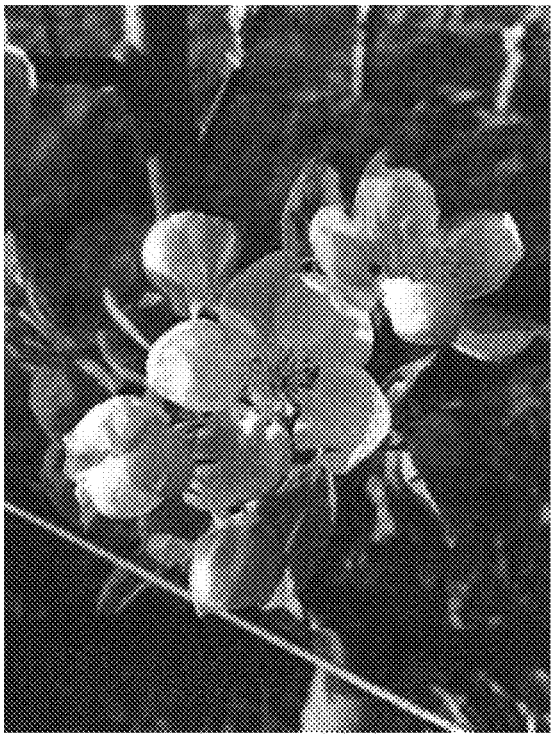
FIG. 6 shows a blossom of 'RDS' on an 'RDS' tree in its third growing season on 'MM106' rootstock; and, FIG. 7 shows the fruit of 'RDS' on an 'RDS' tree in its third growing season on 'MM106' rootstock.
Figure 7:
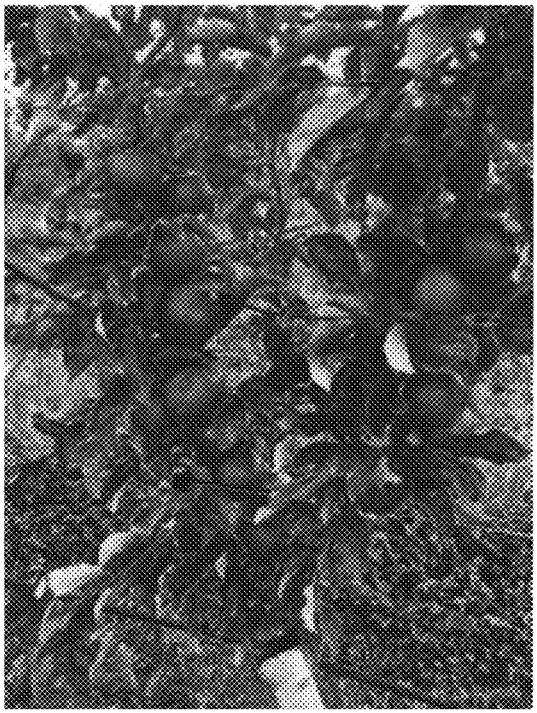

The following-detailed botanical description is based on observations made during the third growing season at Lucaston, Tasmania, Australia of 3-year-old trees planted on 'MM106' rootstock (not patented). The cultivar has not been observed under all possible environmental conditions. The phenotype may vary significantly with variations in the environment such as temperature, length of day and light intensity, without any variance in genotype. It should be understood that the characteristics described will vary somewhat depending upon cultural practices and climatic conditions, and will vary with location and season. The plant and flower quantified measurements and foliage size are expressed as an average of measurements taken from several individual plants of 'RDS' using standard commercial cultural practices. The measurements of any individual plant or any group of plants of 'RDS' may vary from the stated average. All colors are described according to The Royal Horticultural Society Colour Chart ($5^{TH}$ edition 2007).

Tree:

*Vigor*.—Medium.

*Type*.—Ramified — Bearing on Spurs and Long Shoots.

*Habit*.—Spreading.

*Height*.—3.6 m.

*Trunk diameter*.—45 mm at 100 mm above the graft.

*Bark texture*.—Smooth.

*Bark color*.—Reddish-brown 181A on sunny side.

*Branch*.—Fruiting branches located at around 1 m above the graft union.

*Length*.—1.5 m average.

*Diameter*.—18 mm at base.

*Crotch angle*.—Branches on unpruned tree are horizontal.

*Bark color*.—Reddish-brown 181A on sun exposed side.

*Lenticel length*.—0.8 mm to 1.2 mm Average is 1 mm.

*Lenticel color*.—Orange-white 159A.

*Quantity of lenticels per cm*$^2$.—3 to 7 per cm$^2$.

One year old shoot:

*Length*.—205 mm average.

*Color*.—Reddish-brown 181A.

*Pubescence*.—Weak.

*Thickness*.—6.5 mm average.

*Internode length*.—13.3 mm average.

*Number of lenticels per cm*$^2$.—4 to 8 per cm$^2$ on average.

Flower bud:

*Size*.—5.1 mm on average.

*Color*.—Greyed-purple N186C.

*Shape*.—Ovoid.

Flowers:

*Diameter of fully open flower.*—36 mm on average.

*Relative position of petal margin.*—Touching to occasionally free.

*Quantity of flowers per cluster.*—5 to 7.

*Date of beginning of flowering.*—24$^{th}$ of September in Tasmania.

*Date of full bloom.*—30$^{th}$ of September in Tasmania.

*Pollination requirement.*—Pollination required by another diploid variety flowering at similar time.

Petals:

*Quantity per flower.*—5.

*Shape.*—Ovate to ellipsoid.

*Length.*—23 mm.

*Width.*—15.8 mm.

*Apex.*—Ovoid.

*Base.*—Obtuse.

*Margin.*—Smooth.

*Texture.*—Upper surface — Smooth.

*Texture.*—Lower surface — Smooth.

*Color.*—Upper surface — Red-purple RHS 64D.

*Color.*—Lower surface — Red-purple RHS 63C.

*Pistils.*—7.7 mm long; Yellow-green RHS 144C Color.

*Stigma.*—0.5 mm diameter; Yellow-green RHS 144C Color.

*Position of stigma relative to anther.*—Same level.

*Style.*—5 fused at base; Length 6.25 mm; Color 145C Yellow-green; Pubescent at base.

*Ovary.*—Pubescent; 1.51 mm average diameter; Color Yellow-green 144C.

*Anthers.*—19 mm average per flower; Length 2.3 mm; Width 1.9 mm; Ample pollen quantity, Color Yellow 10C.

*Pedicel.*—Length 16.5 mm average; Diameter 1.5 mm; Color: 187C Grey-purple on sun exposed side; 144B Yellow-green on shaded side.

*Sepals.*—Quantity 5; Length 5.8 mm average; Width 4.1 mm average; Color: 59B Red-purple at base with 144B Yellow-green from base to tip with smooth straight margin and pubescent.

*Flower fragrance.*—Absent.

Leaves:

*Length.*—113 mm average.

*Width.*—70 mm average.

*Length/width ratio.*—1.6:1.

*Blade margin.*—Serrate Type 1.

*Shape.*—Oval to obtuse.

*Apex.*—Acute in shape.

*Base.*—Obtuse in shape.

*Pubescence.*—Not pubescent on underside or upper side.

*Color.*—Upper surface — Green N137D.

*Color.*—Lower surface — Green N146B.

*Attitude in relation to shoot.*—Outward.

*Petiole.*—Length 39.5 mm average; Diameter 2.5 mm average; Color: Grey-purple 184A.

*Mid rib.*—Greyed-purple 184A to Yellow-green 145A.

*Leaf vein.*—Extending from base of mid rib Greyed-purple 184A to leaf tip Yellow-green 145A.

*Venation pattern.*—Arcuate from mid rib to Reticulate with smaller veins.

Fruit:

*Quantity per cluster.*—5 to 7 per cluster if no thinning occurs.

*Diameter.*—76.5 mm average.

*Height.*—69.3 mm average.

*Ratio of height to width.*—About 1:0.91.

*General shape in profile.*—Globose.

*Position of maximum diameter.*—Near center.

*Ribbing.*—Moderate.

*Crowning at calyx end.*—Absent or weak.

*Size of eye.*—9.6 mm average.

*Aperture of eye.*—Mostly closed, occasionally open.

*Length of sepal.*—5.2 mm average length.

*Bloom of skin.*—Moderate to strong.

*Greasiness of skin.*—Absent or weak.

*Background color of skin.*—Yellow-green 154D.

*Amount of over color.*—Very large.

*Over color of skin.*—Red-purple 59A.

*Intensity of over color.*—Dark.

*Pattern of over color.*—Solid Flush with weakly defined stripes.

*Amount of russet around stalk cavity.*—Medium to low.

*Amount of russet on cheeks.*—Absent.

*Area of russet around eye basin.*—Absent.

*Length of stalk.*—24.5 mm average.

*Thickness of stalk.*—2.1 mm average.

*Stalk color.*—Greyed-orange 165B.

*Depth of stalk cavity.*—12.1 mm average.

*Width of stalk cavity.*—30.9 mm average.

*Depth of eye basin.*—5.2 mm average.

*Width of eye basin.*—29.1 mm average.

*Flesh color.*—White 155A.

*Firmness of flesh.*—8.3 kg, Firm.

*Flesh texture.*—Firm and crisp.

*Aroma.*—Fresh.

*Juiciness.*—Ample.

*Total soluble solids.*—15° Brix.

*Seeds.*—Minimum of 1, mostly 2 per cell; 8 per fruit; Acute; Greyed-orange 166B; Aperture of locules closed or slightly open.

Harvest:

*Harvest date.*—Time of Eating Maturity — Mid to Late season, Apr. 26, 2018 in Tasmania, Australia.

*Number of picks.*—One.

*Yield.*—21 kg from typical three-year-old tree.

*Average fruit weight.*—189.5 grams.

*Disease/insect resistance/susceptibility.*—No resistance/susceptibility noted. Winter hardiness, cold tolerance, drought, and heat tolerance are similar to parent variety. The fruit coloration is retained in warmer environments.

Market use: Fresh.

We claim:

1. A new and distinct apple tree substantially as described and illustrated herein.

* * * * *